United States Patent [19]

Gunther

[11] Patent Number: 4,903,711
[45] Date of Patent: Feb. 27, 1990

[54] DEVICE FOR PREVENTING INFANT COLIC

[76] Inventor: Roland E. Gunther, R.D. 1 - Box 282, New Berlin, N.Y. 13411

[21] Appl. No.: 260,527

[22] Filed: Oct. 21, 1988

[51] Int. Cl.⁴ ............................................. A61F 13/00
[52] U.S. Cl. .................................... 128/874; 128/875
[58] Field of Search ............... 116/215, 227, DIG. 13; 33/365, 379; 128/87 R, 24 R, DIG. 15, 33, DIG. 20, 75, 76 R, 874, 875; 5/434, 436, 490; 2/49 R; 297/393

[56] References Cited

U.S. PATENT DOCUMENTS

| | | | |
|---|---|---|---|
| 1,648,970 | 11/1927 | Strelow | 128/DIG. 20 |
| 3,009,254 | 11/1961 | Youngs | 33/379 |
| 3,159,924 | 12/1964 | Lieblein | 33/379 |
| 3,164,151 | 1/1965 | Vere Nicoll | 128/87 R |
| 3,522,804 | 8/1970 | Towbin | 128/869 |
| 3,662,057 | 5/1972 | Webster et al. | 128/89 R |
| 3,848,281 | 11/1974 | Mathews | 5/436 |
| 4,521,974 | 6/1985 | Neis et al. | 33/365 |
| 4,617,691 | 10/1986 | Monti et al. | 5/434 |
| 4,738,488 | 4/1988 | Camelio | 5/436 |

*Primary Examiner*—Robert A. Hafer
*Assistant Examiner*—Charles H. Sam
*Attorney, Agent, or Firm*—Donald A. Kettlestrings

[57] ABSTRACT

A device for preventing infant colic and stomach discomfort includes a collar or vest for attachment to the infant and a bubble level is attached to the collar or vest for visually indicating the position of the infant's torso with respect to vertical. The level visually displays a range of desirable positions with respect to vertical for the infant's torso during nursing, and the level displays a range of desirable positions with respect to vertical for the infant's torso during so-called burping procedures for eliminating air from the infant's stomach.

11 Claims, 2 Drawing Sheets

DEVICE FOR PREVENTING INFANT COLIC

This invention relates to a device for preventing infant colic and more particularly to such a device which can be conveniently attached to the infant for visually indicating the position of the infant's torso during nursing and so-called burping of the infant.

Very young infants often suffer from the painful condition known as colic. The most obvious outward sign of the malady is a distressed wailing by the infant which often lasts for over an hour. The condition frequently occurs shortly after eating and ends just before it comes time for the next feeding. Colic is caused by air entrapped in the alimentary canal during and just after feeding, and the discomfort experienced is similar to that of so-called "gas pains".

It is, therefore, an object of the present invention to provide a device for preventing infant colic.

Another object is to provide such a device which enables positioning of the infant during nursing so as to prevent or reduce collection of air in the alimentary canal of the infant.

A further object of the invention is the provision of such a device which enables positioning of the infant during so-called "burping" to most effectively permit release of air trapped in the infant's stomach.

Additional objects and advantages of the invention will be set forth in part in the description which follows, and in part will be obvious from the description or may be learned by practice of the invention. The objects and advantages are realized and attained by means of the instrumentalities and combinations particularly pointed out in the appended claims.

To achieve these and other objects the present invention provides a device for preventing infant colic and stomach discomfort, the device comprising: means for attachment to the infant; and means in operative relationship with the attachment means for visually indicating the position of the infant's torso with respect to vertical.

It is to be understood that both the foregoing general description and the following detailed description are exemplary and explanatory but are not restrictive of the invention.

The accompanying drawings, which are incorporated in and constitute a part of this specification, illustrate an example of a preferred embodiment of the invention and, together with the description, serve to explain the principles of the invention.

Figure 1:
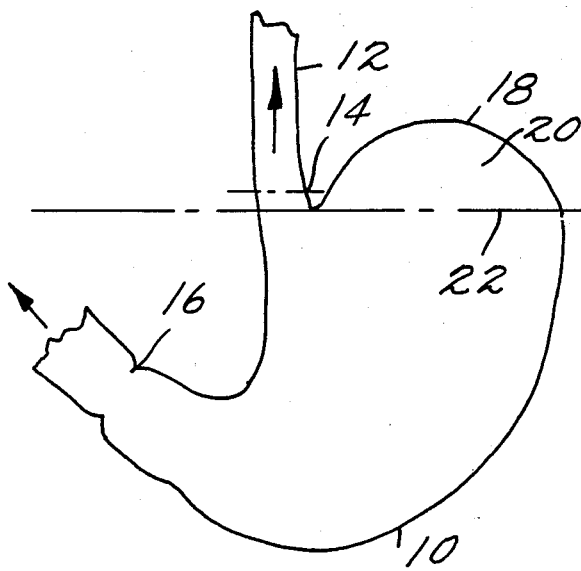
FIG. 1 is a diagrammatic illustration of an infant's stomach when the infant's torso is in a substantially vertical position.

With reference now to the drawings, wherein like reference characters designate like or corresponding parts throughout the several views, there is shown in FIG. 1 a representation of an infant's stomach 10. The esophagus 12, cardiac sphincter 14, pyloric sphincter 16 and fundus 18 are also illustrated.

When the torso of the infant is in a vertical position, as shown in FIG. 1, stomach 10 defines a bulge 20 which extends upwardly from an imaginary horizontal line 22 which extends substantially through cardiac sphincter 14.

Appreciable amounts of air are swallowed by infant's during suckling, and that air collects within bulge 20 of the infant's stomach. In order to relieve the collection of air within bulge 20, it is common practice to "burp" infants after each feeding. However, because bulge 20 extends above imaginary horizontal line 22 when the infant's torso is in a substantially vertical position, not all of the air trapped within bulge 20 can reach the upper opening of the stomach, or cardiac sphincter 14. As a result, a portion of the air remains trapped within bulge 20.

When the infant is then placed into a horizontal position after it has been "burped", the air which still remains within stomach 10 and within bulge 20 can move, along with the stomach contents, through pyloric sphincter 16 into the duodenum, the jejunum and finally into the ilium. This movement of air through the digestive tract of the infant causes discomfort and pain to the infant, and this discomfort and pain is evidenced by the infant's crying.

Figure 2:
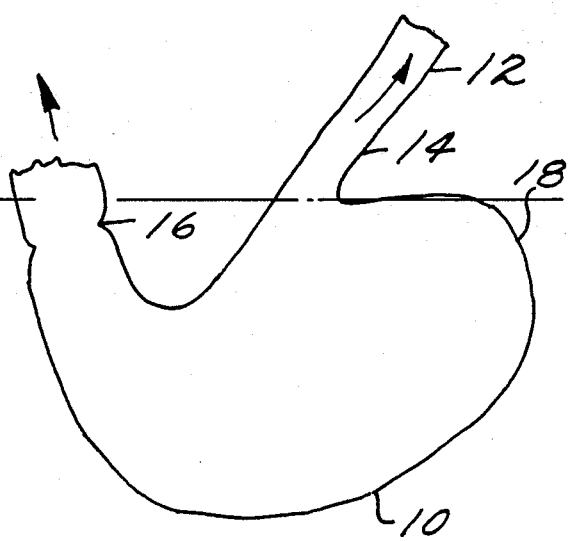
FIG. 2 is a diagrammatic illustration of an infant's stomach when the infant's torso is tilted to the infant's left.
Figure 3:
FIG. 3 is a front elevation view of a collar device worn by an infant in accordance with this invention.
Figure 4:
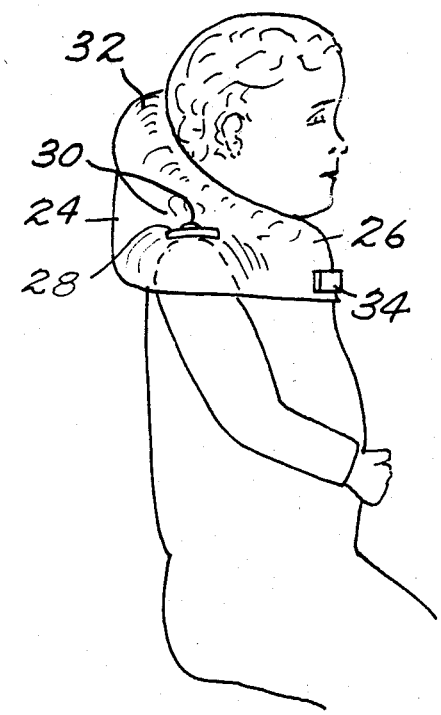
FIG. 4 is a side elevation view of the collar device and infant shown in FIG. 3.
Figure 5:
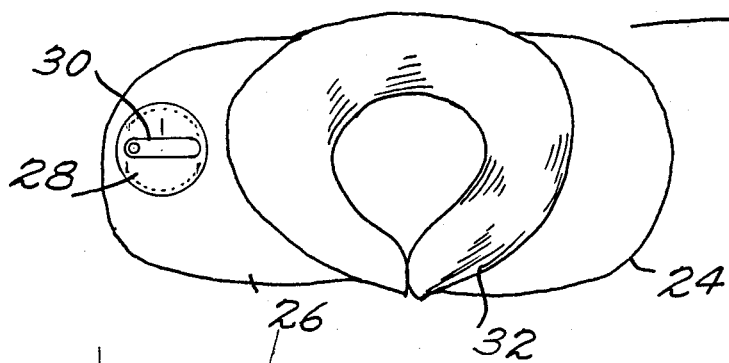
FIG. 5 is a top plan view of the collar device.

In order to help the infant eliminate substantially all of the air from stomach 10 during the "burping" process, it is advisable to tilt the infant slightly to its left so that the highest portion or fundus 18 of bulge 20 in stomach 10 is positioned substantially level with cardiac sphincter 14. This position of stomach 10 is shown in FIG. 2. In this position, even if a small amount of bulge 20 remains above horizontal line 22, little or no air can be trapped within bulge 20 because the stomach undergoes a constant kneading action.

During the time that the infant is being fed and before it is "burped", there is present in the infant's stomach a mixture of air and food. If the infant is fed in a supine position, it is certain that the air-food mixture will come into contact with pyloric sphincter 16. Because the muscles that control pyloric sphincter 16 are not very strong at an early age, the possibility exists of leakage of the air-food mixture through pyloric sphincter 16. Air that enters the intestine cannot be "burped" out.

It is, therefore, important that the infant be fed in an essentially upright position at all times so that the stomach contents which come into contact with pyloric sphincter 16 will be low in air content. If the infant is fed in a substantially upright or vertical position, the hazard of having air pass directly from the infant's mouth via its stomach to its intestine will be substantially eliminated.

Accordingly, device 24 of this invention prevents infant colic and stomach discomfort by guiding and reminding the person feeding the infant to maintain the infant in a substantially vertical position during the feeding process. Device 24 also guides and reminds the person feeding the infant to tilt the infant's torso during the "burping" process so that the maximum amount of air trapped within bulge 20 of stomach 10 can be eliminated through the infant's cardiac sphincter 14.

In accordance with the invention, device 24 includes means 26 for attachment to the infant. Further, device 24 includes means 28 in operative relationship with attachment means 26 for visually indicating the position of the infant's torso with respect to vertical.

Indicating means 28 preferably include a bubble level 30 which visually displays a range of desirable positions from 35 to 33 with respect to vertical for the infant's torso during so-called "burping" procedures for most effectively eliminating air from the infant's stomach. See FIG. 7.

Figure 7:
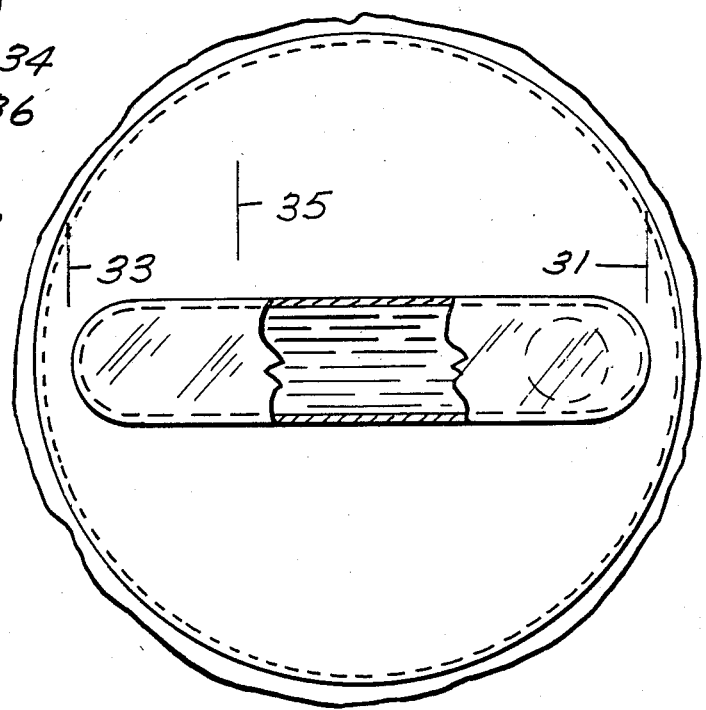
FIG. 7 is a fragmentary top plan view of the bubble level.
Figure 8:
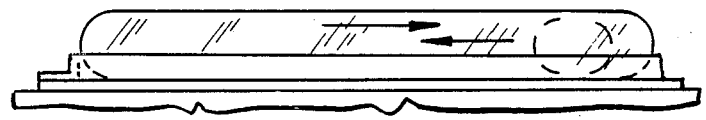
FIG. 8 is a fragmentary front elevation view of the bubble level.

Attachment means 26 are normally attached to the infant for enabling level 30 to display desired leftward leaning positions of the infant's torso with respect to vertical so that the infant can be tilted to the left, as previously described, during the "burping" procedure. Level 30 preferably displays a range of preferred positions for feeding the infant of from vertical to substantially twenty-five degrees from vertical. This range of positions is shown in FIG. 7 as the range between indicia 31 and 33, and this range is satisfactory for feeding because it will prevent air from traveling directly from the infant's mouth through the esophagus and stomach to the infant's intestine.

Level 30 also displays a range of preferred positions for "burping" the infant of from substantially fifteen to twenty-five degrees from vertical. This range of positions is shown in FIG. 7 as the range between indicia 35 and 33, and this range of positions will substantially position bulge 20 of the infant's stomach beneath imaginary horizontal line 22 so as to enable air trapped within bulge 20 to escape through cardiac sphincter 14 and through the infant's esophagus during the "burping" procedure.

Attachment means 26 may preferably include a collar 32 which can be positioned around the infant's neck and which can be fastened by a hook and loop type fastener, such as Velcro, or other conventional means 34. Collar 32 is preferably shaped to support the infant's head in an upright position with respect to the infant's torso. This will relieve the person feeding the infant from the additional task of supporting the infant's head during feeding and "burping" procedures.

Alternately, attachment 26 may include a vest 36 which is removably attachable about the shoulders and torso of the infant. Hook and loop type fastening elements, such as Velcro, or other conventional fastening means 38 can be used to removably attach vest 36 to the infant.

Figure 6:
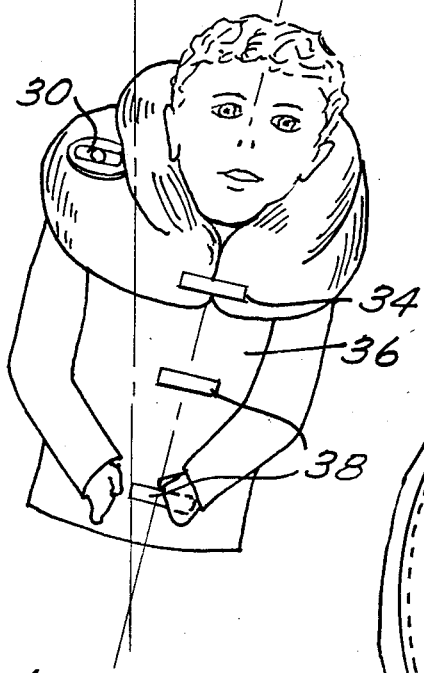
FIG. 6 is a front elevation view of a collar-vest device worn by an infant in accordance with the invention and showing the infant tilted to the infant's left.

Another embodiment may provide for a combination collar and vest which is removably attachable about the neck, shoulders and torso of the infant. See FIG. 6. The collar portion of such a collar-vest combination is preferably shaped to support the infant's head in an upright position with respect to the infant's torso in the same manner as described with respect to collar 32.

In each embodiment, level 30 is attached to the collar or vest to enable the person feeding or "burping" the infant to easily observe level 30 so as to enable that person to maintain the infant in the desired position. Level 30 is constructed so that it will only indicate how far the infant is leaning to its left. Level 30 will not show forward or backward leaning of the child, but forward or backward leaning of the child within a range of approximately ten degrees will not affect the ability of level 30 to indicate leftward leaning of the child. This will obviate the need to maintain the infant in any precise position during the feeding and "burping" procedures. There is no need to position the infant with extreme accuracy. Rather, the results intended will be accomplished if the infant's torso is substantially maintained within the feeding range displayed by level 30 during the feeding process and if the infant's torso is maintained within the "burping" range displayed by level 30 during the "burping" procedure. Level 30 serves as a guide for the person feeding and "burping" the infant and the level also serves as a reminder of the importance of the infant's position during the feeding and "burping" procedures.

The invention in its broader aspects is not limited to the specific details shown and described, and departures may be made from such details without departing from the principles of the invention and without sacrificing its chief advantages.

What is claimed is:

1. A device for preventing infant colic and stomach discomfort, said device comprising:
    means for attachment to said infant; and
    means in operative relationship with said attachment means for visually indicating the position of said infant's torso with respect to vertical, wherein said indicating means include indicia for visually displaying a range of desirable positions with respect to vertical for said infant's torso during nursing by said infant, whereby collection of air in the infant's stomach and intestine can be reduced or avoided.

2. A device as in claim 1 wherein said indicating means further include indicia for visually displaying a range of desirable positions with respect to vertical for said infant's torso during so-called burping procedures for eliminating air from the infant's stomach.

3. A device as in claim 2 wherein said attachment means are normally attached to said infant for enabling said indicating means to display desired leftward leaning positions of said infant's torso with respect to vertical.

4. A device as in claim 3 wherein said indicating means include a bubble level.

5. A device as in claim 4 wherein said level displays a range of preferred positions for feeding said infant of from vertical to twenty-five degrees from vertical.

6. A device as in claim 5 wherein said level displays a range of preferred positions for burping said infant of from fifteen to twenty-five degrees from vertical.

7. A device as in claim 6 wherein said attachment means include a collar removably attachable about the neck of said infant.

8. A device as in claim 7 wherein said collar is shaped to support said infant's head in an upright position with respect to said infant's torso.

9. A device as in claim 6 wherein said attachment means include a vest removably attachable about the shoulders and torso of said infant.

10. A device as in claim 6 wherein said attachment means include a combination collar and vest removably attachable about the neck, shoulders and torso of said infant.

11. A device as in claim 10 wherein said collar portion of said collar and vest combination is shaped to support said infant's head in an upright position with respect to said infant's torso.

* * * * *